US009045738B2

(12) United States Patent
Yamanaka et al.

(10) Patent No.: US 9,045,738 B2
(45) Date of Patent: Jun. 2, 2015

(54) METHOD FOR PRODUCING INDUCED PLURIPOTENT STEM CELLS AND METHOD FOR CULTURING THE SAME

(75) Inventors: Shinya Yamanaka, Kyoto (JP); Kazutoshi Takahashi, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 89 days.

(21) Appl. No.: 13/322,445

(22) PCT Filed: May 28, 2010

(86) PCT No.: PCT/JP2010/059493
§ 371 (c)(1),
(2), (4) Date: Nov. 23, 2011

(87) PCT Pub. No.: WO2010/137746
PCT Pub. Date: Dec. 2, 2010

(65) Prior Publication Data
US 2012/0070896 A1 Mar. 22, 2012

Related U.S. Application Data

(60) Provisional application No. 61/182,542, filed on May 29, 2009.

(51) Int. Cl.
*C12N 5/071* (2010.01)
*C12N 5/074* (2010.01)

(52) U.S. Cl.
CPC .......... *C12N 5/0696* (2013.01); *C12N 2502/00* (2013.01); *C12N 2510/00* (2013.01); *C12N 2502/13* (2013.01); *C12N 2502/1323* (2013.01); *C12N 2501/602* (2013.01); *C12N 2501/603* (2013.01); *C12N 2501/604* (2013.01); *C12N 2501/606* (2013.01)

(58) Field of Classification Search
CPC ............. C12N 2502/13; C12N 5/0696; C12N 2502/00; C12N 2510/00; C12N 2501/604; C12N 2501/603; C12N 2501/602
See application file for complete search history.

(56) References Cited

U.S. PATENT DOCUMENTS 8,278,104 B2    10/2012    Yamanaka et al.

FOREIGN PATENT DOCUMENTS

JP    2005-218306 A    8/2005
WO    WO 2007/069666 A1    6/2007

OTHER PUBLICATIONS

Stadtfeld. Science, 322: 945-949, 2008.*
Okita. Science, 322: 949-953, 2008.*
Gonzalez. PNAS, 106(22): 8918-8922, 2009.*
Hanley et al., British Journal of Hæmatology, 151: 16-24, 2010.*
Oliveri et al. Regenerative Medicine, 2(5): 795-816, Sep. 2007.*
Djuric and Ellis, 202, Stem Cell Research and Therapy, 2010,1:3.*
Kim et al. Cell Stem Cell, 4(6): 472-476, 2009.*
Miyamoto. Biology of Reproduction, 80: 935-943, 2009.*
Wade et al. Eur. J. Biochem., 269:2284-2287, 2002.*
Gurdon & Colman. Nature, 402:743-746, 1999.*
Lim et al. Proteomics, 2:1187-1203, 2002.*
Prowse et al. Proteomics, 5:978-989, 2005.*
Lu et al. PNAS, 103(15): 5688-5693, 2006.*
Oh et al. Clin. and Exp. Pharmacology and Physiology, 33:489-495, 2006.*
Ludwig et al. Nat. Biotech., 24(2): 185-187, 2006.*
Xu et al. (Nature Biotech.;19: 971-974, 2001.*
Conner, Current Protocols in Molecular Biology, 23.2.1-23.2.7, 2000.*
Martin, M.J. et al., Human embryonic stem cells express an immunogenic nonhuman sialic acid, Nat. Med., vol. 11, No. 2, pp. 228-232, 2005.
Park, J.H. et al., Establishment and Maintenance of Human Embryonic Stem Cells on STO, a Permanently Growing Cell Line, Bio. Reprod., 69, pp. 2007-2014, 2003.
Park, SP. et al., Establishment of human embryonic stem cell lines from frozen—thawed blastocysts using STO cell feeder layers, Hum. Reprod., vol. 19, No. 3, pp. 676-684, 2004.
Richards, M. et al., Human feeders support prolonged undifferentiated growth of human inner cell masses and embryonic stem cells, Nat. Biotechnol., vol. 20, pp. 933-936, 2002.
Richards, M. et al., Comparative Evaluation of Various Human Feeders for Prolonged Undifferentiated Growth of Human Embryonic Stem Cells, Stem Cells, vol. 21, pp. 546-556, 2003.
Takahashi, K. et al., Induction of Pluripotent Stem Cells from Mouse Embryonic and Adult Fibroblast Cultures by Defined Factors, Cell, 126 (4), pp. 663-676, 2006.
Xu, C. et al., Immortalized Fibroblast-Like Cells Derived from Human Embryonic Stem Cells Support Undifferentiated Cell Growth, Stem Cells, vol. 22, pp. 972-980, 2004.
International Search Report in PCT Application No. PCT/JP2010/059493 dated Sep. 7, 2010 in 2 pages.
International Preliminary Report on Patentability in PCT/JP2010/059493 dated Nov. 29, 2011 in 6 pages.
Bigdeli N. et al., "Adaptation of human embryonic stem cells to feeder-free and matrix-free culture conditions directly on plastic surfaces", J. Biotechnol., Jan. 2008, vol. 133, No. 1, pp. 146-153.
Stewart M.H. et al. "Clonal isolation of hESCs reveals heterogeneity within the pluripotent stem cell compartment", Nat. Methods, Oct. 2006, vol. 3, No. 10, pp. 807-815.
Stojkovic, P. et al., "An autogenic feeder cell system that efficiently supports growth of undifferentiated human embryonic stem cells", Stem Cells, Mar. 2005, vol. 23, No. 3, pp. 306-314.
Takahashi, K. et al., "Human induced pluripotent stem cells on autologous feeders", PLoS ONE, Dec. 2009, vol. 4, No. 12, e8067 in 6 pages.

(Continued)

*Primary Examiner* — Thaian N Ton
(74) *Attorney, Agent, or Firm* — Knobbe, Martens, Olson & Bear, LLP

(57) ABSTRACT

Induced pluripotent stem cells are produced from human somatic cells by co-culturing human somatic cells having a reprogrammed nucleus with human cells as feeder cells. Induced pluripotent stem cells are produced from somatic cells by co-culturing somatic cells having a reprogrammed nucleus with autologous cells as feeder cells. Induced pluripotent stem cells are cultured with culture supernatant of somatic cells.

5 Claims, 10 Drawing Sheets

(56) References Cited

OTHER PUBLICATIONS

Takahashi, K. et al., "Induction of pluripotent stem cells from adult human fibroblasts by defined factors", Cell, Nov. 2007, vol. 131, No. 5, pp. 861-872.

Nakagawa et al., "Generation of induced pluripotent stem cells without Myc from mouse and human fibroblasts," *Nature Biotechnology*, vol. 26(1), pp. 101-106 (Jan. 2008).

European Search Report in PCT/JP2010059493 dated Nov. 13, 2013.

Mallon, et al. "Induction of pluripotent stem cells from adult human fibroblasts by defined factors," *The International Journal of Biochemistry & Cell Biology*, vol. 38, pp. 1063-1075 (Jan. 2006).

Rodriguez-Piza, et al. "Reprogramming of human fibroblasts to induced pluripotent stem cells under xeno-free conditions," *Stem Cells*, vol. 28, pp. 36-44 (2009).

Unger, et al. "Immortalized human skin fibroblast feeder cells support growth and maintenance of both human embryonic and induced pluripotent stem cells," *Human Reproduction*, vol. 24(10), pp. 2567-2581 (Oct. 2009).

\* cited by examiner 1388-iPS1

1392-iPS1

1503-iPS1

NHDF-iPS1

SEQUENCE LISTING

<160> NUMBER OF SEQ ID NOS: 32

<210> SEQ ID NO 1
<211> LENGTH: 24
<212> TYPE: DNA
<213> ORGANISM: Artificial sequence
<220> FEATURE:
<223> OTHER INFORMATION: primer

<400> SEQUENCE: 1
gacaggggga ggggaggagc tagg                                          24

<210> SEQ ID NO 2
<211> LENGTH: 26
<212> TYPE: DNA
<213> ORGANISM: Artificial sequence
<220> FEATURE:
<223> OTHER INFORMATION: primer

<400> SEQUENCE: 2
cttccctcca accagttgcc ccaaac                                        26

<210> SEQ ID NO 3
<211> LENGTH: 26
<212> TYPE: DNA
<213> ORGANISM: Artificial sequence
<220> FEATURE:
<223> OTHER INFORMATION: primer

```
<400> SEQUENCE: 3
gggaaatggg aggggtgcaa aagagg                                           26

<210> SEQ ID NO 4
<211> LENGTH: 26
<212> TYPE: DNA
<213> ORGANISM: Artificial sequence
<220> FEATURE:
<223> OTHER INFORMATION: primer

<400> SEQUENCE: 4
ttgcgtgagt gtggatggga ttggtg                                           26

<210> SEQ ID NO 5
<211> LENGTH: 26
<212> TYPE: DNA
<213> ORGANISM: Artificial sequence
<220> FEATURE:
<223> OTHER INFORMATION: primer

<400> SEQUENCE: 5
ccctggtgcc gtgaagctgg agaagg                                           26

<210> SEQ ID NO 6
<211> LENGTH: 28
<212> TYPE: DNA
<213> ORGANISM: Artificial sequence
<220> FEATURE:
<223> OTHER INFORMATION: primer

<400> SEQUENCE: 6
tactggttcg ctttctcttt cgggcctg                                         28

<210> SEQ ID NO 7
<211> LENGTH: 25
<212> TYPE: DNA
<213> ORGANISM: Artificial sequence
<220> FEATURE:
<223> OTHER INFORMATION: primer

<400> SEQUENCE: 7
acgacgtgag cgccctgcag tacaa                                            25

<210> SEQ ID NO 8
<211> LENGTH: 25
<212> TYPE: DNA
<213> ORGANISM: Artificial sequence
<220> FEATURE:
<223> OTHER INFORMATION: primer

<400> SEQUENCE: 8
gctggagctg gcctcggact tgacc                                            25

<210> SEQ ID NO 9
<211> LENGTH: 23
<212> TYPE: DNA
<213> ORGANISM: Artificial sequence
<220> FEATURE:
<223> OTHER INFORMATION: primer

<400> SEQUENCE: 9
tctctcctct tccttcctcc atg                                              23

<210> SEQ ID NO 10
```

```
<211> LENGTH: 25
<212> TYPE: DNA
<213> ORGANISM: Artificial sequence
<220> FEATURE:
<223> OTHER INFORMATION: primer

<400> SEQUENCE: 10
ctgtttgtag ctgaggttca ggatg                                  25

<210> SEQ ID NO 11
<211> LENGTH: 26
<212> TYPE: DNA
<213> ORGANISM: Artificial sequence
<220> FEATURE:
<223> OTHER INFORMATION: primer

<400> SEQUENCE: 11
cctgctcaag ctgactcgac accgtg                                 26

<210> SEQ ID NO 12
<211> LENGTH: 25
<212> TYPE: DNA
<213> ORGANISM: Artificial sequence
<220> FEATURE:
<223> OTHER INFORMATION: primer

<400> SEQUENCE: 12
ggaaaagctg gccctggggt ggagc                                  25

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
aaatgcgttt ctcgttgctt                                        20

<210> SEQ ID NO 14
<211> LENGTH: 20
<212> TYPE: DNA
<213> ORGANISM: Artificial sequence
<220> FEATURE:
<223> OTHER INFORMATION: primer

<400> SEQUENCE: 14
gccacaggcc aatagtttgt                                        20

<210> SEQ ID NO 15
<211> LENGTH: 20
<212> TYPE: DNA
<213> ORGANISM: Artificial sequence
<220> FEATURE:
<223> OTHER INFORMATION: primer

<400> SEQUENCE: 15
acaggttggt gtgggttcat                                        20

<210> SEQ ID NO 16
<211> LENGTH: 20
<212> TYPE: DNA
<213> ORGANISM: Artificial sequence
<220> FEATURE:
<223> OTHER INFORMATION: primer

<400> SEQUENCE: 16
```

```
ctgcatcttc caaagcatca                                                    20

<210> SEQ ID NO 17
<211> LENGTH: 28
<212> TYPE: DNA
<213> ORGANISM: Artificial sequence
<220> FEATURE:
<223> OTHER INFORMATION: primer

<400> SEQUENCE: 17
acccattatc cagatgtgtt tgcccgag                                           28

<210> SEQ ID NO 18
<211> LENGTH: 26
<212> TYPE: DNA
<213> ORGANISM: Artificial sequence
<220> FEATURE:
<223> OTHER INFORMATION: primer

<400> SEQUENCE: 18
atggtgaagc tgggcatagg cggcag                                             26

<210> SEQ ID NO 19
<211> LENGTH: 30
<212> TYPE: DNA
<213> ORGANISM: Artificial sequence
<220> FEATURE:
<223> OTHER INFORMATION: primer

<400> SEQUENCE: 19
attcttcgtt gtcaagccgc caaagtggag                                         30

<210> SEQ ID NO 20
<211> LENGTH: 30
<212> TYPE: DNA
<213> ORGANISM: Artificial sequence
<220> FEATURE:
<223> OTHER INFORMATION: primer

<400> SEQUENCE: 20
agttgtttgc tgcggagttg tcatctcgtc                                         30

<210> SEQ ID NO 21
<211> LENGTH: 20
<212> TYPE: DNA
<213> ORGANISM: Artificial sequence
<220> FEATURE:
<223> OTHER INFORMATION: primer

<400> SEQUENCE: 21
accacagtcc atgccatcac                                                    20

<210> SEQ ID NO 22
<211> LENGTH: 20
<212> TYPE: DNA
<213> ORGANISM: Artificial sequence
<220> FEATURE:
<223> OTHER INFORMATION: primer

<400> SEQUENCE: 22
tccaccaccc tgttgctgta                                                    20

<210> SEQ ID NO 23
<211> LENGTH: 20
<212> TYPE: DNA
```

```
<213> ORGANISM: Artificial sequence
<220> FEATURE:
<223> OTHER INFORMATION: primer

<400> SEQUENCE: 23
caatgtggcc gaggactttg                                                   20

<210> SEQ ID NO 24
<211> LENGTH: 22
<212> TYPE: DNA
<213> ORGANISM: Artificial sequence
<220> FEATURE:
<223> OTHER INFORMATION: primer

<400> SEQUENCE: 24
cattctcctt agagagaagt gg                                                22

<210> SEQ ID NO 25
<211> LENGTH: 20
<212> TYPE: DNA
<213> ORGANISM: Artificial sequence
<220> FEATURE:
<223> OTHER INFORMATION: primer

<400> SEQUENCE: 25
ttgccagcca ttatcattca                                                   20

<210> SEQ ID NO 26
<211> LENGTH: 20
<212> TYPE: DNA
<213> ORGANISM: Artificial sequence
<220> FEATURE:
<223> OTHER INFORMATION: primer

<400> SEQUENCE: 26
tatagagctg ctgcgggatt                                                   20

<210> SEQ ID NO 27
<211> LENGTH: 20
<212> TYPE: DNA
<213> ORGANISM: Artificial sequence
<220> FEATURE:
<223> OTHER INFORMATION: primer

<400> SEQUENCE: 27
gagaagggcg tgagagagtg                                                   20

<210> SEQ ID NO 28
<211> LENGTH: 20
<212> TYPE: DNA
<213> ORGANISM: Artificial sequence
<220> FEATURE:
<223> OTHER INFORMATION: primer

<400> SEQUENCE: 28
aaacagccag tgcaggagtt                                                   20

<210> SEQ ID NO 29
<211> LENGTH: 20
<212> TYPE: DNA
<213> ORGANISM: Artificial sequence
<220> FEATURE:
<223> OTHER INFORMATION: primer

<400> SEQUENCE: 29
gatttgtggg cctgaagaaa                                                   20
```

```
<210> SEQ ID NO 30
<211> LENGTH: 20
<212> TYPE: DNA
<213> ORGANISM: Artificial sequence
<220> FEATURE:
<223> OTHER INFORMATION: primer

<400> SEQUENCE: 30
ggaaaaaggg gtttccagag                                             20

<210> SEQ ID NO 31
<211> LENGTH: 24
<212> TYPE: DNA
<213> ORGANISM: Artificial sequence
<220> FEATURE:
<223> OTHER INFORMATION: primer

<400> SEQUENCE: 31
agggttcggg ggaggtaagg gtgc                                        24

<210> SEQ ID NO 32
<211> LENGTH: 24
<212> TYPE: DNA
<213> ORGANISM: Artificial sequence
<220> FEATURE:
<223> OTHER INFORMATION: primer

<400> SEQUENCE: 32
agggttgcgt gcgtaaagcc ggag                                        24
```

US 9,045,738 B2

METHOD FOR PRODUCING INDUCED PLURIPOTENT STEM CELLS AND METHOD FOR CULTURING THE SAME

TECHNICAL FIELD

The present invention relates to a method for producing induced pluripotent stem cells. The present invention also relates to a method for culturing induced pluripotent stem cells and a culture medium for culturing induced pluripotent stem cells.

BACKGROUND ART

Induced pluripotent stem cells (iPS cells) can be prepared by introduction of nuclear reprogramming factors to somatic cells (K. Takahashi and S. Yamanaka, Cell 126 (4), p663, 2006; WO2007/069666). The iPS cells are usually established and cultured using as feeder cells mouse embryonic fibroblasts (MEFs) whose growth was inactivated by mitomycin C or g-ray irradiation. However, cells derived from a different species are used, so there is a possibility that the obtained iPS cells may have an unknown virus or pathogen. Therefore, in some cases, usage of iPS cells established and cultured by a conventional method is not suitable for human therapy. It has been reported that sialic acid which is not produced in human cells was detected on the surface of human embryonic stem cells (ES cells) cultured using MEFs as feeder cells (Martin, M J. et al. Nat. Med. 11, p228, 2005).

It has been reported, so far, that self-replication of human ES cells was maintained by culture using as feeder cells human fibroblasts derived from neonatal foreskin or fibroblast-like cells derived from ES cells (Richards, S. et al. Nat Biotechnol. 20, p933, 2002; Park, J H. et al. Bio. Reprod. 69, p2007, 2003; Park, S P. et al. Hum Reprod. 19, p676, 2004; Richards, M. et al. Stem Cells 21, p546, 2003; and Xu, C. et al. Stem Cells 22, p972, 2004), but there has been no report of a successful case with iPS cells.

Further, it is difficult to completely remove feeder cells from iPS cells cultured together with feeder cells. In therapies using iPS cells, it is necessary to reduce the risk of contamination of cells from a different species and other individuals. Thus, a technology to allow usage of cells of the same species or autologous cells in the entire process of establishment and culture of iPS cells is demanded.

DISCLOSURE OF THE INVENTION

An object of the present invention is to provide a technology for production of safer iPS cells. Another object of the present invention is to provide a more efficient technology for culturing iPS cells.

The inventors of the present invention intensively studied to solve the above objects. As a result, they succeeded in production of iPS cells from human somatic cells by co-culturing human somatic cells to which nuclear reprogramming factors were introduced, with human somatic cells as feeder cells. Further, iPS cells were successfully produced from somatic cells by co-culturing the somatic cells to which nuclear reprogramming factor were introduced, with autologous cells as feeder cells. Further, they also discovered that iPS cells can be efficiently cultured by using the culture supernatant of somatic cells, thereby the present invention was completed.

An aspect of the present invention is to provide a method for producing induced pluripotent stem cells from somatic cells, comprising co-culturing somatic cells having a reprogrammed nucleus with autologous cells as feeder cells.

Another aspect of the present invention is to provide the method as described above, which comprises the steps of:
a) introducing a nuclear reprogramming factor(s) to first somatic cells; and
b) co-culturing the first somatic cells to which the nuclear reprogramming factor(s) has/have been introduced, with second somatic cells which have the same origin as the first somatic cells but no nuclear reprogramming factor is introduced.

Another aspect of the present invention is to provide a method for producing induced pluripotent stem cells from human somatic cells, comprising co-culturing human somatic cells having a reprogrammed nucleus with human cells as feeder cells.

Another aspect of the present invention is to provide the method as described above, which comprises the steps of:
c) introducing a nuclear reprogramming factor(s) to first human somatic cells; and
d) co-culturing the first human somatic cells to which the nuclear reprogramming factor(s) has/have been introduced, with second somatic cells as feeder cells, which are derived from human but no nuclear reprogramming factor is introduced.

Another aspect of the present invention is to provide the method as described above, wherein said nuclear reprogramming factor is at least one selected from the group consisting of the Oct genes, Sox genes, Klf genes, Myc genes, Nanog gene, Sall genes and Lin genes.

Another aspect of the present invention is to provide the method as described above, wherein said nuclear reprogramming factor is at least one selected from the group consisting of the Oct3/4 gene, Sox2 gene, Klf4 gene, c-Myc gene, L-Myc gene, Nanog gene, Sall4 gene and Lin28 gene.

Another aspect of the present invention is to provide the method as described above, wherein said nuclear reprogramming factors are the Oct3/4 gene, Sox2 gene, Klf4 gene and c-Myc gene.

Another aspect of the present invention is to provide the method as described above, wherein said somatic cells are fibroblasts.

Another aspect of the present invention is to provide the method as described above, wherein said feeder cells are cells treated with mitomycin C or γ-ray irradiation.

Another aspect of the present invention is to provide a method for culturing induced pluripotent stem cells, comprising co-culturing induced pluripotent stem cells with human somatic cells as feeder cells.

Another aspect of the present invention is to provide the method as described above, wherein said human somatic cells are derived from the same individual as the human somatic cells from which said induced pluripotent stem cells were induced.

Another aspect of the present invention is to provide the method as described above, wherein said human somatic cells are fibroblasts.

Another aspect of the present invention is to provide the method as described above, comprising treating said somatic cells with mitomycin C or γ-ray irradiation.

Another aspect of the present invention is to provide a method for culturing induced pluripotent stem cells, comprising culturing induced pluripotent stem cells with culture supernatant of somatic cells.

Another aspect of the present invention is to provide the method as described above, wherein said somatic cells are human somatic cells.

Another aspect of the present invention is to provide the method as described above, wherein said human somatic cells are derived from the same individual as that the human somatic cells from which said induced pluripotent stem cells were induced.

Another aspect of the present invention is to provide the method as described above, wherein said somatic cells are fibroblasts.

Another aspect of the present invention is to provide the method as described above, wherein said induced pluripotent stem cells are human induced pluripotent stem cells.

Another aspect of the present invention is to provide a culture medium for culturing induced pluripotent stem cells, wherein said culture medium comprises culture supernatant of human somatic cells.

Another aspect of the present invention is to provide the culture medium as described above, wherein said human somatic cells are human fibroblasts.

According to the method of the present invention, safe iPS cells can be produced. Further, according to the culturing method of the present invention, iPS cells can be efficiently cultured.

DESCRIPTION OF THE PREFERRED EMBODIMENTS

Figure 1:
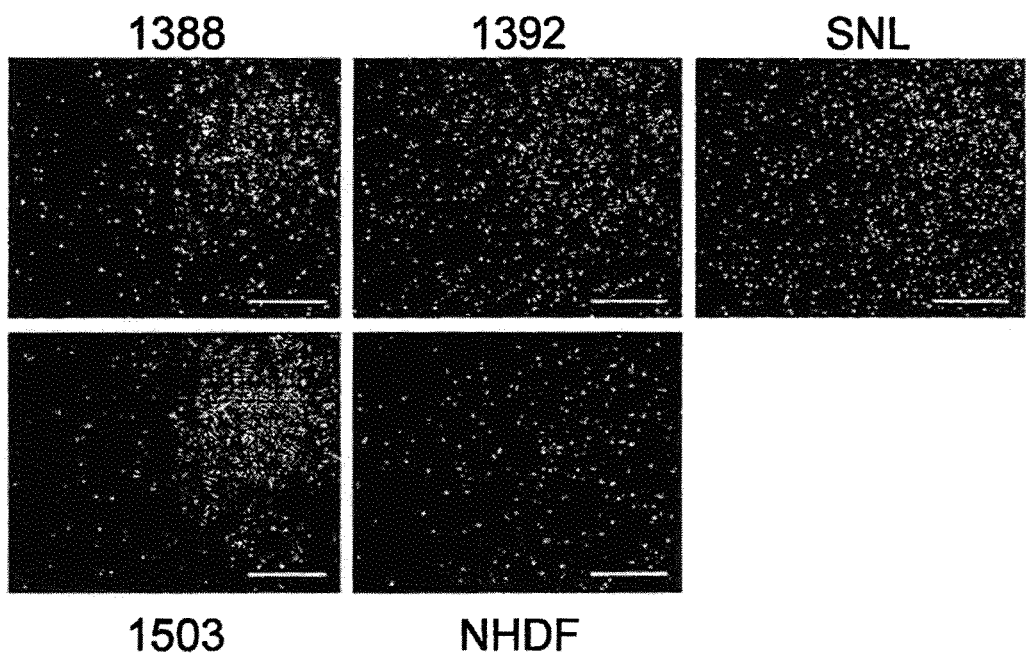
FIG. 1 shows micrographs of mitomycin C-treated human dermal fibroblasts (HDFs: NHDFs, 1388, 1392 and 1503) and STO cell-derived cells (SNL). The bar represents 200 μm.

The preferred embodiments of the present invention will now be described.

Unless otherwise explained, methods described in standard protocols such as J. Sambrook, E. F. Fritsch & T. Maniatis (Ed.), Molecular Cloning, Laboratory Manual (3rd edition), Cold Spring Harbor Press, Cold Spring Harbor, N.Y. (2001); F. M. Ausubel, Brent, R. E. Kingston, D. D. Moore, J. G. Seidman, J. A. Smith, K. Struhl (Ed.), Current Protocols in Molecular Biology, John Wiley & Sons Ltd., or modified or altered methods thereof can be employed. When commercially available reagent kits or measurement devices are employed, protocols described in attached instructions may be used unless otherwise specified.

The purposes, characteristics, advantages and ideas of the present invention are clear to those skilled in the art by descriptions in the present specification, and according to the descriptions in the present specification, they can easily reproduce the present invention. The modes and particular examples of the present invention described below represent preferred embodiments of the present invention and are shown for illustration or explanation, and the present invention is not limited thereto. It is clear to those skilled in the art that various alterations and modifications may be carried out according to the descriptions in the present specification, within the intention and the scope of the present invention disclosed in the present specification.

Production Method of Induced Pluripotent Stem Cells

The present invention provides a method for producing induced pluripotent stem cells (iPS cells) from somatic cells, which method comprises a step of co-culturing somatic cells whose nucleus was reprogrammed, with autologous cells as feeder cells.

The above production method preferably comprises the following steps:

a) introducing a nuclear reprogramming factor(s) to first somatic cells; and b) co-culturing the first somatic cells to which the nuclear reprogramming factor(s) has/have been introduced, with second somatic cells as feeder cells, which second somatic cells have the same origin as the first somatic cells but no nuclear reprogramming factor is introduced.

The present invention also provides a method for producing iPS cells from human somatic cells, comprising a step of co-culturing human somatic cells having a reprogrammed nucleus with human cells as feeder cells.

The above production method preferably comprises the following steps:

c) introducing a nuclear reprogramming factor(s) to first human somatic cells; and d) co-culturing the first human somatic cells to which the nuclear reprogramming factor(s) has/have been introduced, with second somatic cells as feeder cells, which second somatic cells are derived from human but no nuclear reprogramming factor is introduced.

In the present specification, "iPS cells" means cells having pluripotency and self-replication ability, which have been artificially induced by reprogramming cells other than germ-line cells (e.g., egg cells, spermatids, oogonia and spermatogonia, and progenitor cells thereof) and undifferentiated cells derived from embryos in early developmental stages (e.g., embryonic stem cells). Hereinafter, "cells other than germ-line cells and undifferentiated cells derived from embryos in early developmental stages" are referred to as somatic cells.

The somatic cells may be derived from an embryo, fetus or adult, and may be derived from any animal species such as mouse or human, and are preferably derived from human. The properties thereof are not limited as long as they are cells lacking at least a part of the totipotency retained by fertilized cells, and examples of the somatic cells include fibroblasts, epithelial cells and hepatocytes.

"Feeder cells" means cells which are different from the cells of interest and used for adjusting culture conditions of the cells of interest, and play an auxiliary role. The feeder cells in the present invention are used to support self-replication of iPS cells.

"Autologous cells" means cells which have the same origin as the cells of interest. Autologous cells are derived from the same individual as the somatic cells from which iPS cells have been induced, and the type of the tissue from which they are derived is not limited. For example, they are somatic cells used for induction of the iPS cells.

Examples of the nuclear reprogramming factor(s) include reprogramming factors described in U.S. Pat. Nos. 8,440, 461; 8,278,104; 8,183,038; 8,129,187; 8,058,065; 8,048,999; 7,964,401; 7,615,374; and US Pre-Grant Publications Nos: 2013/0059386A1; 2011/0236971A2; 2011/0028537A1; 2010/0261274A1; 2010/0216236A1; 2010/0210014A1; 2010/0062533A1; 2010/0015705A1; 2009/0227032A1; 2009/0081784A1; 2009/0068742A1; 2009/0047263A1; and 2008/0233610A1. More particularly, products from genes selected from the Oct gene family, Klf genes, Sox gene family, Myc gene family, Sall gene family, Nanog gene and Lin gene family are included therein.

Here, examples of the genes belonging to the Oct gene family include Oct3/4 (mouse NM_013633, human NM_002701), Oct1A (mouse NM_198934, human NM_002697), Oct6 (mouse NM_011141, human NM_002699); examples of the genes belonging to the Klf gene family include Klf1 (mouse NM_010635, human NM_006563), Klf2 (mouse NM_008452, human NM_016270), Klf4 (mouse NM_010637, human NM_004235) and Klf5 (mouse NM_009769, human NM_001730); examples of the genes belonging to the Sox gene family include Sox1 (mouse NM_009233, human NM_005986), Sox2 (mouse NM_011443, human NM_003106), Sox3 (mouse NM_009237, human NM_005634), Sox17 (mouse NM_011446, human NM_031439), Sox15 (mouse NM_009235, human NM_006942), Sox17 (mouse NM_011441, human NM_022454) and Sox18 (mouse NM_009236, human NM_018419); examples of the genes belonging to the Myc gene family include c-Myc (mouse NM_010849, human NM_002467), N-Myc (mouse NM_008709, human NM_005378) and L-Myc (mouse NM_008506, human NM_001033081); examples of the genes belonging to the Sall gene family include Sall1 (mouse NM_021390, human NM_002968) and Sall4 (mouse NM_175303, human NM_020436); and examples of the genes belonging to the Lin gene family include Lin28 (mouse NM_145833, human NM_024674) and Lin28b (mouse NM_001031772, human NM_001004317).

More preferred nuclear reprogramming factors are the Oct3/4 gene, Klf4 gene, Sox2 gene, c-Myc gene, L-Myc gene, Sall4 gene, Sall1 gene, Nanog gene (JP 2005-110565A) and Lin28 gene. As the nuclear reprogramming factor(s), products from other genes may be introduced, and examples thereof include immortalization-inducing factors.

These genes were exemplified by sequences of mouse and human with the accession numbers of National Center for Biotechnology Information, but, since they are genes highly conserved among vertebrates, they may also be the genes of other animals, and include homologues thereof. Genes having variations such as polymorphisms are also included in the nuclear reprogramming factor genes as long as these have functions equivalent to the products of the wild-type genes.

Reprogramming may be carried out by introduction of at least one of the above-described reprogramming factors, and a plurality of the reprogramming factors may be used in combination. The number of the reprogramming factors to be included is 2, 3, preferably 4, or more. More preferred combinations are the combination of the Oct3/4 gene, Sox2 gene and Klf4 gene; and the combination of the Oct3/4 gene, Sox2 gene, Klf4 gene and c-Myc gene.

For introducing the reprogramming factor(s), when the nuclear reprogramming factor(s) is/are a protein(s) which function(s) in a cell, it is preferred to incorporate the gene(s) encoding the protein(s) into an expression vector and introduce the expression vector into differentiated cells of interest such as somatic cells to allow expression of the gene(s) in the cells (gene introduction method). The expression vector is not limited, and examples thereof include plasmid vectors, virus vectors and artificial chromosome vectors (Suzuki N et al., J Biol Chem. 281(36):26615, 2006), and examples of the virus vectors include adenovirus vectors, Sendai virus vectors, retrovirus vectors and lentivirus vectors. Further, the nuclear reprogramming factor(s) may be introduced into cells by binding the factor(s) to a peptide called Protein Transduction Domain (PTD) to be added to the culture medium (Protein Transduction method). In addition, methods for introduction of the nuclear reprogramming factor(s) to cells using various protein-introducing reagents (e.g., Chariot™ or Bioporter™) may be exemplified. In the case of a protein secreted to the outside of the cell, the factor(s) may be added to the culture medium for the differentiated cells upon preparation of induced pluripotent stem cells. In cases where a part of the nuclear reprogramming factor(s) is/are expressed in the somatic cells to be reprogrammed, the protein(s) is/are not required to be externally introduced.

In some cases, a cytokine and/or compound is/are added in order to substitute the nuclear reprogramming factor(s) or to increase the introduction efficiency, and examples of the cytokine include the SCFs (stem cell factors), bFGF, WNT genes and LIFs (leukemia inhibitory factors), and examples of the compound include the Histone Deacetylase inhibitors, DNA methylation inhibitors, MEK inhibitors, GSK3β inhibitors TGFβ receptor inhibitors and ROCK inhibitors.

After the introduction of the reprogramming factor(s) into somatic cells, the cells are preferably cultured in a culture medium for human ES cells in the case of using human somatic cells. Here, the culture medium for human ES cells is not limited and preferably the DMEM/F12 medium containing 20% serum substitute, 2 mM L-glutamine, $1 \times 10^{-4}$ M non-essential amino acids, $1 \times 10^{-4}$ M 2-mercaptoethanol, 0.5% penicillin and streptomycin, and 4 ng/ml recombinant human basic fibroblast growth factor (bFGF). When the cells are cultured in a culture medium for human ES cells, the cells after introduction of the reprogramming factor(s) may be cultured in an exchanged culture medium, or recultured, after separation of the cells, at an appropriate cell density. The cell density is not limited but preferably about $1 \times 10^{4}$ cells/cm$^2$.

Subsequently, the somatic cells (first somatic cells) to which the nuclear reprogramming factor(s) has/have been introduced are isolated and cultured together with somatic cells (second somatic cells) to which the nuclear reprogramming factor(s) is/are not introduced (hereinafter referred to as somatic cells for feeders). Here, it is preferred to culture the somatic cells (second somatic cells) for feeders in advance and then add the somatic cells (first somatic cells) to which the nuclear reprogramming factor(s) has/have been introduced thereto. It is preferable that the somatic cells (second somatic cells) for feeders are used in excess with respect to the somatic cells (first somatic cells) to which the nuclear reprogramming factor(s) has/have been introduced. The ratio is preferably not less than 1:4, more preferably not less than 1:5. The growth capacity of the somatic cells for feeders is preferably inactivated by, for example, mitomycin C or γ-ray irradiation.

To support self-replication of iPS cells, a gene may be introduced to the feeder cells such that an exogenous cytokine such as SCF, bFGF, WNT gene or LIF is secreted.

When the somatic cells (first somatic cells) to which the nuclear reprogramming factor(s) has/have been introduced are isolated to be co-cultured with the somatic cells (second somatic cells) for feeders, ES cell-like colonies are appropriately selected and subcultured with somatic cells (second somatic cells). As other modes of the selection method, there are a method wherein cells expressing undifferentiation marker genes are selected and a method wherein cells are selected based on cell morphology. The method wherein cells expressing undifferentiation marker genes are selected is not limited, and for example, a reporter gene may be knocked-in in the downstream of the promoter of each undifferentiation marker gene, followed by selecting cells expressing the marker gene. Further, the transcription product may be detected by the PCR method, LAMP method, Northern hybridization method or the like, or the translation product may be detected by the RIA method, IRMA method, EIA method, ELISA method, LPIA method, CLIA method, immunoblotting method or the like. Here, the undifferentiation marker gene is not limited, and it is a gene expressed specifically in ES cells, and examples thereof include the genes expressed specifically in ES cells described in WO2005/080598, WO2007/069666, WO2008/118820, WO2009/057831 and Nat Biotechnol. 25, 803, 2007. It is preferably selected from the group consisting of Oct3/4, Sox2, Nanog, Lin28, Rex1, UTF1, Eras, Fgf4, TDGF, Cripto, Dad, ESG1, GDF3, Sall4, Fbx15 SSEA-1, SSEA-4, TRA-1-60, TRA-1-81 or alkaline phosphatase (e.g., TRA-2-54 or TRA-2-49), depending on the animal species (for example, SSEA-1 is specific to mouse, and SSEA-4, TRA-1-60 and TRA-1-81 are specific to human). Examples of the reporter gene include the genes encoding fluorescent proteins such as the green-fluorescent protein (GFP), yellow-fluorescent protein (YFP) and blue-fluorescent protein (BFP); photoproteins such as aequorin; and enzymes such as β-galactosidase, alkaline phosphatase, horseradish peroxidase (HRP) and luciferase.

The thus produced iPS cells may be used as the material for cell replacement therapy.

Method for Culturing Induced Pluripotent Stem Cells

The present invention also provides a method for culturing iPS cells using human somatic cells as feeder cells. Here, the type of the human somatic cells is not limited as long as the cells can aid self-replication of iPS cells, and preferably a human fibroblast strain. Here, the iPS cells are derived from any animal species such as mouse or human, and are preferably derived from human. The human somatic cells are preferably those obtained from the individual from which the iPS cells are derived. More preferably, they are the same somatic cells as those used for establishment of the iPS cells. The growth capacity of the human somatic cells used as the feeder cells is preferably inactivated by, for example, mitomycin C or g-ray irradiation.

To support self-replication of the iPS cells, a gene may be introduced to the somatic cells used as the feeder cells such that an exogenous cytokine is secreted. Examples of the cytokine include SCF, bFGF, WNT genes or LIF.

As another mode, the present invention also provides a method for culturing iPS cells using a culture medium containing the culture supernatant of human somatic cells. The culture medium is preferably the culture supernatant of human somatic cells cultured in a culture medium for human ES cells. Here, the culture medium for human ES cells is not limited, and preferably a culture medium for mammalian cells (e.g., the DMEM/F12 medium) containing a serum substitute (e.g., KSR, Invitrogen), L-glutamine, non-essential amino acids, 2-mercaptoethanol, penicillin and streptomycin. The concentration of each component of the culture medium and additives therefor may be appropriately adjusted by those skilled in the art, and a recombinant human basic fibroblast growth factor (bFGF) is preferably added thereto immediately before use. The type of the human somatic cells used for preparation of the culture supernatant is not limited as long as the somatic cells can aid self-replication of iPS and preferably a human fibroblast strain. The human somatic cells are preferably obtained from the individual from whom the iPS cells are derived. They are more preferably somatic cells used when the iPS cells have been established.

The culture supernatant is prepared, for example, by culturing the somatic cells at an appropriate cell density for not less than 1 day, followed by removal of the cells from the culture medium. Preferably, the culture supernatant is obtained by 1 day of culturing followed by exchanging the culture medium, culturing for additional 1 day and removing the cells. The cell density in the culture medium used to obtain the culture supernatant is preferably not less than $1 \times 10^5$ cells/ml.

The culture medium may contain the culture supernatant in an amount sufficient for aiding self-replication of iPS cells, and preferably contains not less than 10% thereof. More preferably, it is a culture medium containing the culture supernatant in an amount of not less than 50%, 80% or 90%. Still more preferably, the culture medium is the culture supernatant itself. The compounds other than the above-described culture supernatant in the culture medium of the present invention for iPS cells are not limited as long as they do not inhibit growth of iPS cells, and components of a normal culture medium for mammalian cells or the like may be added.

EXAMPLES

The examples and comparative examples of the present invention will be described, but the examples merely show modes of the present invention for the purpose of supporting the reproducibility of the present invention, and the present invention is not limited thereto.

Methods
Cell Culture

Human dermal fibroblasts (HDFs) were purchased from Cell application Inc. HDF, 293T and PLAT-E were cultured using Dulbecco's modified Eagle medium (DMEM, Nacalai Tesque) supplemented with 10% fetal bovine serum (FBS, Invitrogen), 0.5% penicillin and streptomycin. Human iPS cells were cultured using a medium (culture medium for hES cells) comprising DMEM/F12 (Invitrogen), 20% serum substitute (KSR, Invitrogen), 2 mM glutamine (Invitrogen), $1 \times 10^{-4}$ M non-essential amino acids (Invitrogen), $1 \times 10^{-4}$ M 2-mercaptoethanol, 0.5% penicillin/streptomycin, and 4 ng/ml recombinant human basic fibroblast growth factor (bFGF, Wako Pure Chemicals).

Preparation of iPS Cells iPS cells were established from HDFs by a conventional method (Takahashi, K. et al. Cell 131, 861, 2007) which was modified to some extent. Briefly, the murine solute carrier family 7 (cationic amino acid transporter, y+ system), member 1 (Slc7a1) gene encoding the ecotropic retrovirus receptor was introduced to HDFs by a lentivirus, and the HDFs were plated at $2 \times 10^5$ cells/60-mm dish and incubated overnight. On the next day, Oct3/4, Sox2, Klf4 and c-Myc were introduced by a retrovirus. Six days later, the cells were collected by trypsin treatment and replated at $5 \times 10^5$ cells/100-mm dish. On the next day, the culture medium was exchanged with a culture medium for hES cells and the cells were cultured for 20 days. Twenty five days after the introduction of the genes, ES cell-like colonies were picked up and replated on the fibroblast cells from which they were derived. This replating was counted as 1 passage.

Feeder Cells

Phosphate buffer (PBS, Nacalai Tesque) supplemented with 12 μg/ml mitomycin C was added to near-confluent fibroblast cells, and the resultant was incubated at 37° C. for 3 hours. Thereafter, the cells were washed twice with PBS and collected by trypsin treatment. The cells were plated at $1 \times 10^6$ cells per 24-well plate, 6-well plate, three 60-mm dishes or 100-mm dish.

Culture Supernatant

Fibroblast cells were plated at $3 \times 10^5$ cells per 60-mm dish, and incubated overnight. On the next day, the culture medium was exchanged with 3 ml of a culture medium for hES cells, and the resultant was incubated for 24 hours. Thereafter, the culture supernatant of the fibroblast cells was collected and filtered. To the resulting filtrate, 4 ng/ml bFGF was added immediately before use.

Induction of Differentiation

The iPS cells were treated with a solution (CTK solution) containing 0.1 mg/ml collagenase IV (Invitrogen), 0.25% trypsin, 0.1 mM $CaCl_2$ (Nacalai Tesque) and 20% KSR and collected, and cell clumps were suspended in a culture medium for hES cells which was supplemented with 10 μM Y-27632 (ROCK inhibitor, Wako Pure Chemicals) but did not contain bFGF. The suspended cells were transferred to an Ultra low binding plate (Corning). After 8 days of suspension culture, embryoid bodies were transferred to a gelatin-coated plate, followed by additional 8 days of culture. This incubation was followed by fixation of the cells with PBS supplemented with 4% paraformaldehyde, and the cells were then incubated with PBS supplemented with 5% normal goat antibody or donkey serum (Chemicon), 1% bovine serum albumin (Nacalai Tesque), and 0.2% TritonX-100. The primary antibodies were as follows: anti-SOX17 (1:300, R & D systems), anti-α-smooth muscle actin (1:500, α-SMA, DAKO) and anti-βIII-tubulin (1:1000, Sigma). The secondary antibodies were as follows: Cyanine 3-labeled anti-goat IgG (1:500, Zymed) and Alexa 546-labeled anti-mouse IgG (1:500, Invitrogen). Nuclei were stained with 1 μg/ml Hoechst 33342 (Invitrogen).

Expression Analysis

RT-PCR was carried out according to a conventional method. Briefly, the cells were lysed with Trizol reagent (Invitrogen), and total RNA was extracted. The RNA samples were treated with Turbo DNA free (Ambion) to remove genomic DNA. Reverse transcription was carried out with 1 μg of the DNase-treated RNA using Rever tra ace-α-(Toyobo) and Oligo dT20 primer. Quantitative PCR was carried out using SYBR Premix Ex Taq II (Takara). The sequences of the primers are shown in Table 1.

TABLE 1

| Gene | Sequence (5' to 3') |
| --- | --- |
| OCT3/4 (Endogenous) | GAC AGG GGG AGG GGA GGA GCT AGG (SEQ ID NO: 1) <br> CTT CCC TCC AAC CAG TTG CCC CAA AC (SEQ ID NO: 2) |
| SOX2 (Endogenous) | GGG AAA TGG GAG GGG TGC AAA AGA GG (SEQ ID NO: 3) <br> TTG CGT GAG TGT GGA TGG GAT TGG TG (SEQ ID NO: 4) |
| OCT3/4 (Total) | CCC TGG TGC CGT GAA GCT GGA GAA GG (SEQ ID NO: 5) <br> TAC TGG TTC GCT TTC TCT TTC GGG CCT G (SEQ ID NO: 6) |
| SOX2 (Total) | ACG ACG TGA GCG CCC TGC AGT ACA A (SEQ ID NO: 7) <br> GCT GGA GCT GGC CTC GGA CTT GAC C (SEQ ID NO: 8) |

TABLE 1-continued

| Gene | Sequence (5' to 3') |
|---|---|
| NANOG | TCT CTC CTC TTC CTT CCT CCA TG (SEQ ID NO: 9)<br>CTG TTT GTA GCT GAG GTT CAG GAT G (SEQ ID NO: 10) |
| TERT | CCT GCT CAA GCT GAC TCG ACA CCG TG (SEQ ID NO: 11)<br>GGA AAA GCT GGC CCT GGG GTG GAG C (SEQ ID NO: 12) |
| AFP | AAA TGC GTT TCT CGT TGC TT (SEQ ID NO: 13)<br>GCC ACA GGC CAA TAG TTT GT (SEQ ID NO: 14) |
| PDGFR | ACA GGT TGG TGT GGG TTC AT (SEQ ID NO: 15)<br>CTG CAT CTT CCA AAG CAT CA (SEQ ID NO: 16) |
| PAX6 | ACC CAT TAT CCA GAT GTG TTT GCC CGA G (SEQ ID NO: 17)<br>ATG GTG AAG CTG GGC ATA GGC GGC AG (SEQ ID NO: 18) |
| NAT1 | ATT CTT CGT TGT CAA GCC GCC AAA GTG GAG (SEQ ID NO: 19)<br>AGT TGT TTG CTG CGG AGT TGT CAT CTC GTC (SEQ ID NO: 20) |
| G3PDH | ACC ACA GTC CAT GCC ATC AC (SEQ ID NO: 21)<br>TCC ACC ACC CTG TTG CTG TA (SEQ ID NO: 22) |
| ACTB | CAA TGT GGC CGA GGA CTT TG (SEQ ID NO: 23)<br>CAT TCT CCT TAG AGA GAA GTG G (SEQ ID NO: 24) |

Methylation Analysis

By sonication, 4 µg of genomic DNA was sheared, followed by boiling at 95° C. for 10 minutes. The sheared genomic DNA was incubated with pan-mouse IgG magnetic beads-conjugated anti-5-methyl cytosine antibody (Eurogentec) supplemented with 5 µg/ml BSA and 25 µg/ml yeast tRNA (Ambion) at 4° C. overnight. The beads were washed 3 times with PBS supplemented with 0.05% TritonX-100 and incubated at 65° C. for 5 minutes. Elution by addition of 0.15 ml 1% SDS/1E was repeated. The eluted solution was treated with protease K for 2 hours at 50° C. and subjected to extraction with phenol/chloroform/isoamylalcohol, followed by purification by ethanol precipitation. The primers are shown in Table 2.

TABLE 2

| OCT3/4-ChIP | TTG CCA GCC ATT ATC ATT CA (SEQ ID NO: 25)<br>TAT AGA GCT GCT GCG GGA TT (SEQ ID NO: 26) |
|---|---|
| SOX2-ChIP | GAG AAG GGC GTG AGA GAG TG (SEQ ID NO: 27)<br>AAA CAG CCA GTG CAG GAG TT (SEQ ID NO: 28) |
| NANOG-ChIP | GAT TTG TGG GCC TGA AGA AA (SEQ ID NO: 29)<br>GGA AAA AGG GGT TTC CAG AG (SEQ ID NO: 30) |

TABLE 2-continued

| NAT1-ChIP | AGG GTT CGG GGG AGG TAA GGG TGC (SEQ ID NO: 31)<br>AGG GTT GCG TGC GTA AAG CCG GAG (SEQ ID NO: 32) |
|---|---|

Flow Cytometry

The cells were collected with PBS supplemented with 2 mM EDTA and washed with PBS. With chicken anti-Neu5Gc (1.5 µg/100 µl) antibody and Dylight 488-conjugated donkey anti-chicken IgY antibody (1:100, Jackson Immunoresearch) for staining, $1 \times 10^5$ cells were incubated. Measurement was carried out using FACS Aria (Beckton Dickinson).

Example 1

Figure 2:
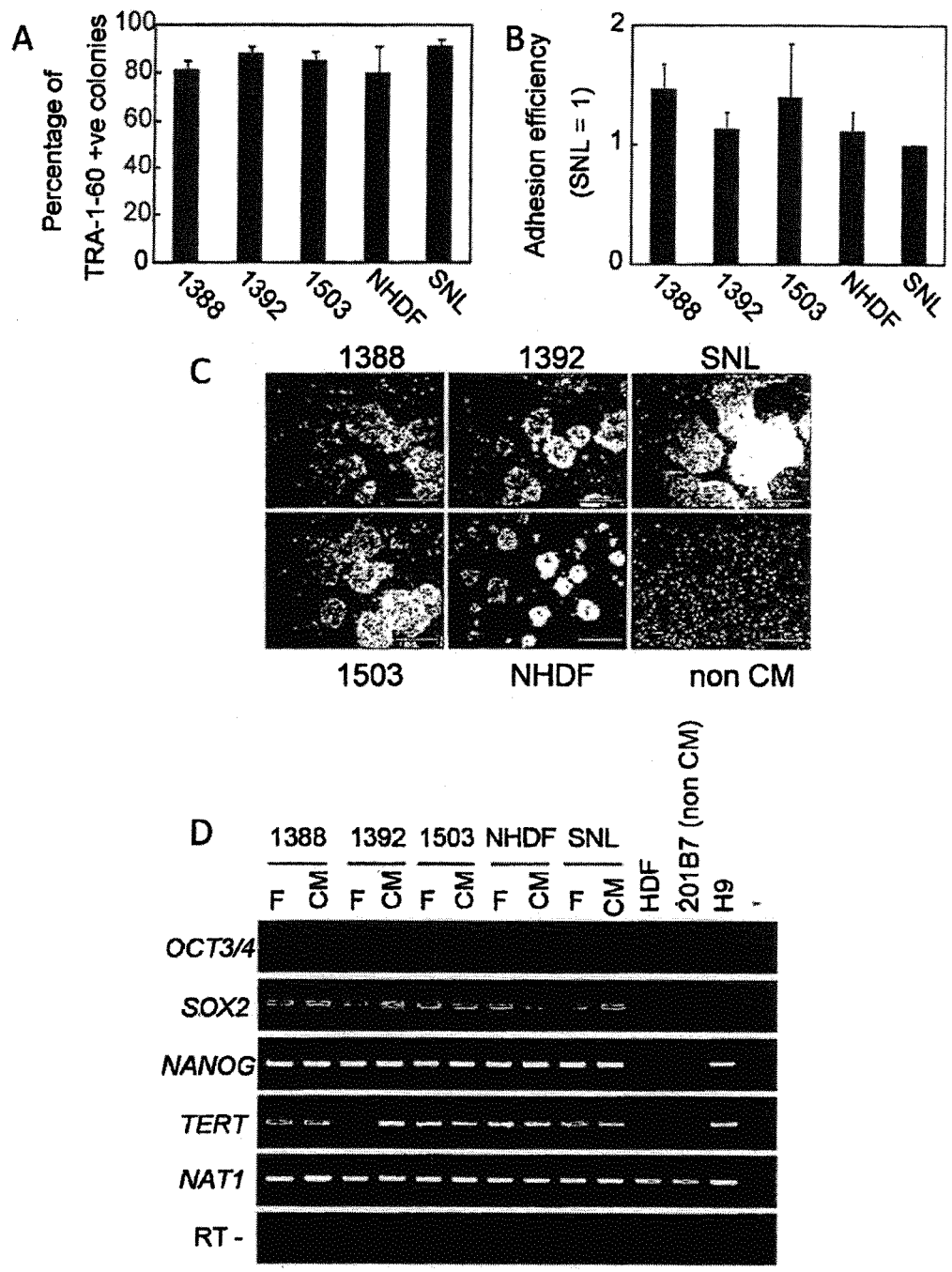
FIG. 2A is a graph showing the content of TRA-1-60-positive colonies observed when 1388-derived iPS cells (201B7) were co-cultured with HDFs or SNL as feeder cells. The analysis was repeated 3 times, and the average is shown in the graph. The error bars represent standard deviation.
FIG. 2B is a graph showing comparison between the colony number when SNL cells were used as feeder cells and the colony number when human fibroblasts of each type were used as feeder cells. The analysis was repeated 3 times, and the average is shown in the graph. The error bars represent standard deviation.
FIG. 2C shows micrographs of iPS cells observed when they were cultured using the culture supernatant of the fibroblasts of the respective types. The bar represents 200 μm.
FIG. 2D is a photograph showing RT-PCR analysis of undifferentiation markers after culturing of iPS cells on feeders (F) or in culture supernatant (CM) (micrographs). As controls, HDFs, H9 (ES cells) and 201B7 (non CM) co-cultured with SNL as feeder cells are shown.

Four human fibroblast strains (NHDF, 1388, 1392 and 1503: neonate, 36 years old female, 56 years old male and 73 years old female, respectively) and SNL (STO cell-derived cells) were treated with mitomycin C and plated on culture plates (FIG. 1). Subsequently, an iPS cell strain derived from 1388 (201B7: WO2009/057831) was plated on each of the above-described fibroblasts at a standard concentration (iPS cells:fibroblasts=1:5). As a result, the 5 types of fibroblasts aided undifferentiation-maintenance culture of the iPS cells, as feeder cells. The contents of TRA-1-60-positive cell colonies were equivalent among the cases where the respective fibroblasts and SNL were used (FIG. 2A). There were no differences in the adhesion efficiencies among the iPS cells on the respective fibroblasts (FIG. 2B).

Figure 3:
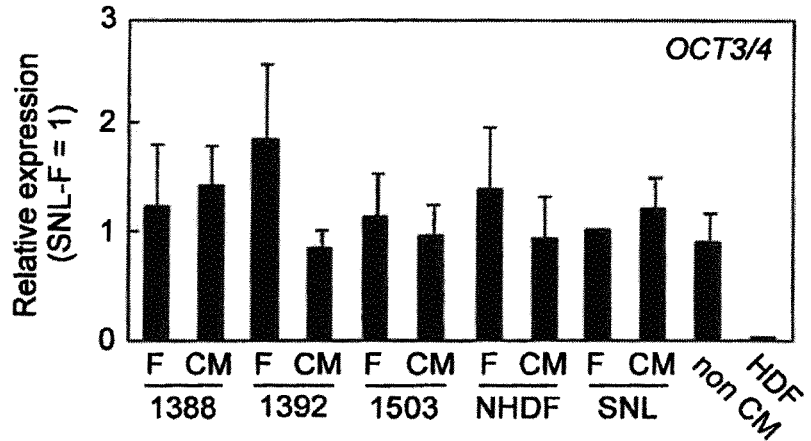
FIG. 3 shows quantitative PCR analysis of undifferentiation markers (A: Oc3/4, B: Sox2, C: Nanog) after culturing of iPS cells (201B7) on feeder cells (F) or in the culture supernatant (CM) of the feeder cells. The data were normalized using G3PDH. The graph shows the average values of three experiments. The error bars represent standard deviation. As controls, HDFs, and 201B7 (non CM) co-cultured with SNL as feeder cells are shown.
Figure 3:
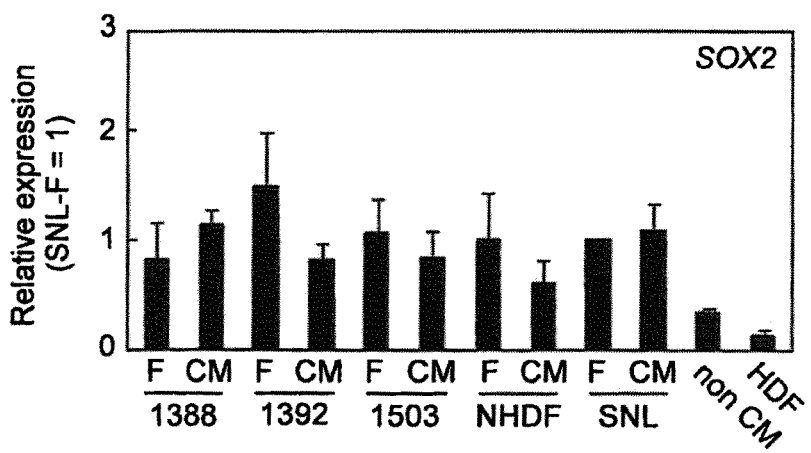
Figure 3:
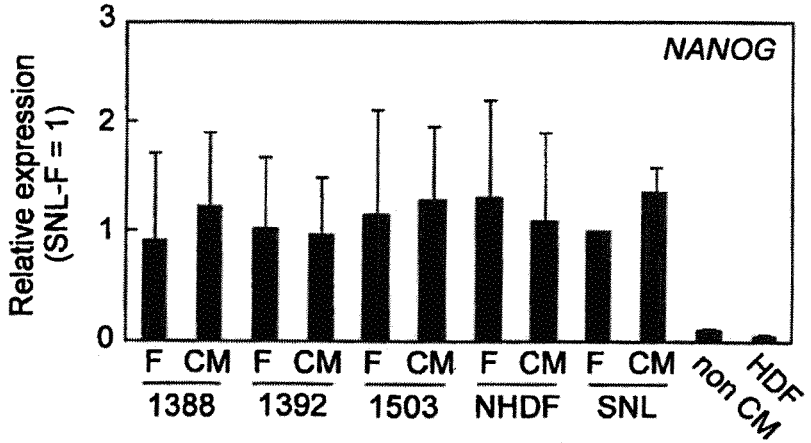

Subsequently, to study whether self-replication of iPS cells is possible even in cases where they are cultured using the culture supernatant of fibroblast cells, iPS cells (201B7) were cultured using a plate coated with Matrigel, in the culture supernatant of each type of fibroblasts or SNL, or in a control medium (non CM) supplemented with bFGF. As a result, in the control medium, there was no formation of cohesive colonies, while in each culture supernatant, an undifferentiated ES cell-like morphology was observed (FIG. 2C). By RT-PCR, expressions of undifferentiated ES cell-specific marker genes (Oct3/4, Sox2, Nanog and TERI) were confirmed in each type of the iPS cells after the culture (FIG. 2D). Also in quantitative PCR, there was no change in the amount of expression of each of the above-described undifferentiated ES cell-specific marker genes (FIG. 3). From the above data, it was shown that neonatal and adult fibroblasts are suitable as feeder cells for iPS cells.

Example 2

To study whether human iPS cells can be established on human fibroblasts, 4 nuclear reprogramming factors (Oct3/4, Sox2, Klf4 and c-Myc) were introduced to human fibroblasts (NHDF, 1388, 1392 and 1503) by a retrovirus. Six days after the introduction, the above cells ($5 \times 10^5$ cells) were transferred to a dish (100 mm) without feeder cells and cultured under conditions for human ES cells. During the culture, the cells became confluent and exhibited a feeder cell-like morphology. Two weeks after the introduction, ES cell-like colonies appeared on cells exhibiting a fibroblast-like morphology. Twenty five days after the introduction, ES cell-like colonies (FIG. 4A) were picked up and co-cultured with mitomycin C-treated parent fibroblasts as feeder cells.

Figure 4:
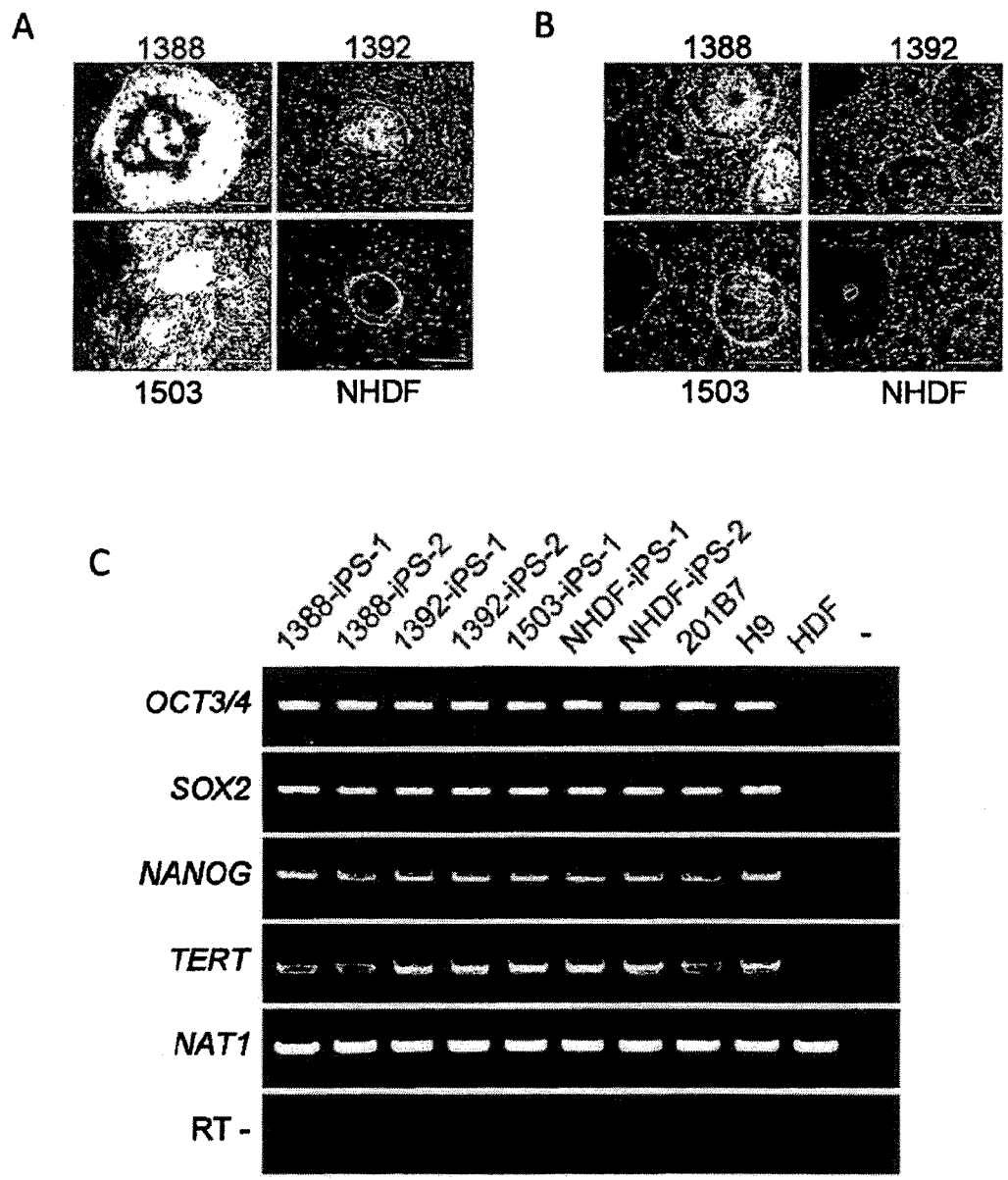
FIG. 4A shows micrographs of early iPS cell colonies. Four factors were introduced to 1388, 1392, 1503 or NHDFs. The micrographs show colonies observed 25 days after the introduction.
FIG. 4B shows micrographs of the respective iPS cell clones established. Each iPS cell clone was cultured on the fibroblasts from which it was derived. The micrographs show cells observed after 3 passages. The bar represents 200 μm.
FIG. 4C is a photograph showing RT-PCR analysis of markers for undifferentiated ES cells in each established iPS cell clone. Each iPS cell clone was cultured on the fibroblasts from which it was derived. As controls, HDFs, H9 and 201B7 co-cultured with SNL as feeder cells are shown.

Between the culture with the SNL-derived fibroblasts (Isogenic) and the culture with the culture supernatants of the SNL-derived fibroblasts (feeder-free), there were no differences in the number of ES cell-like colonies (Table 3). The iPS cells derived from the 4 types of fibroblasts used in Example 1 could be cultured while maintaining their undifferentiated state, by using autologous cells as feeder cells (FIG. 4B).

TABLE 3

|      | SNL     |       | Isogenic |       | feeder-free |       |
|------|---------|-------|----------|-------|-------------|-------|
|      | ES-like | Total | ES-like  | Total | ES-like     | Total |
| 1388 | 5       | 79    | 4        | 62    | 2           | 3     |
| 1392 | 8       | 629   | 16       | 269   | 8           | 334   |
| 1503 | 70      | 408   | 76       | 359   | 58          | 264   |
| NHDF | 26      | 44    | 18       | 39    | 7           | 24    |

Example 3

The amounts of transcription of Oct3/4, Sox2, Nanog and TERT in the iPS cell clones established in Example 2 were confirmed by RT-PCR, and it was shown that these were equivalent to those in H9 (ES cells) and 201B7 (iPS cells) cultured using SNL as feeder cells (FIG. 4C).

Figure 5:
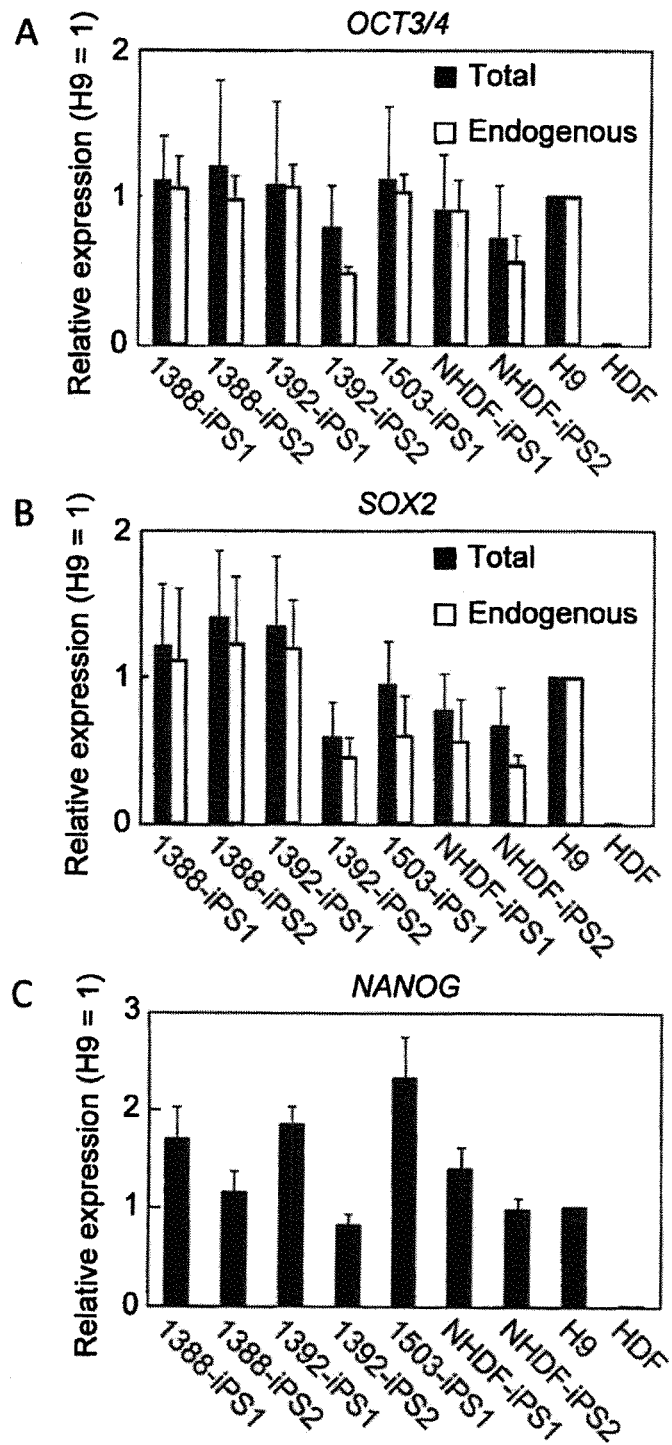
FIG. 5 shows quantitative PCR analysis of undifferentiation markers (A: Oct3/4, B: Sox2, C: Nanog) in: iPS cells established using autologous cells as feeder cells; ES cells (E9); and HDFs. Filled symbols represent the total gene expression and open symbols represent only endogenous gene expression. The data were normalized using G3PDH and calculated using H9 as a standard. The graph shows the average values of three experiments. The error bars represent standard deviation.

As a result of investigation of the total amount of expression and the amount of endogenous expression of Oct3/4 and Sox2 by quantitative PCR, it was confirmed that transcription from the retrovirus vector was silenced (FIG. 5).

Figure 6:
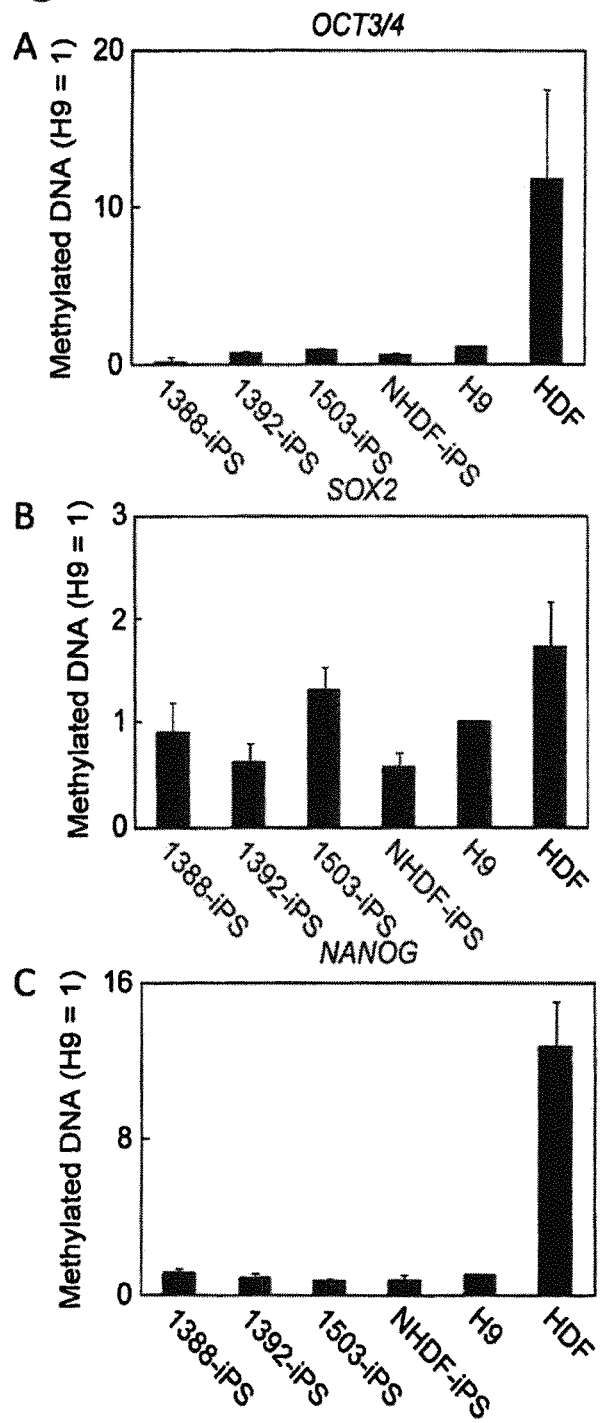
FIG. 6 shows analysis of the methylation levels in the promoter regions of undifferentiation markers (A: Oct3/4, B: Sox2, C: Nanog) of: iPS cells established using autologous cells as feeder cells; ES cells (E9); and HDFs. The ordinate indicates the relative value of methylated DNA calculated using H9 as a standard. The graph shows the average values of three experiments. The error bars represent standard deviation.

Further, methylation of the promoter regions of pluripotency-related genes such as Oct3/4 and Nanog in the iPS cells maintained and established using the autologous cells as feeder cells was investigated by immunoprecipitation using the anti-methylation cytosine antibody, and it was confirmed to be equivalent to that in H9 (ES cells) (FIG. 6). On the other hand, the upstream of each of Wnt5A, IGF2 and Slc5A4 in the above iPS cells was highly methylated. From these data, it was suggested that iPS cells established on the fibroblasts from which they were derived have the same properties as iPS cells or ES cells established on conventional murine fibroblasts.

Figure 7:
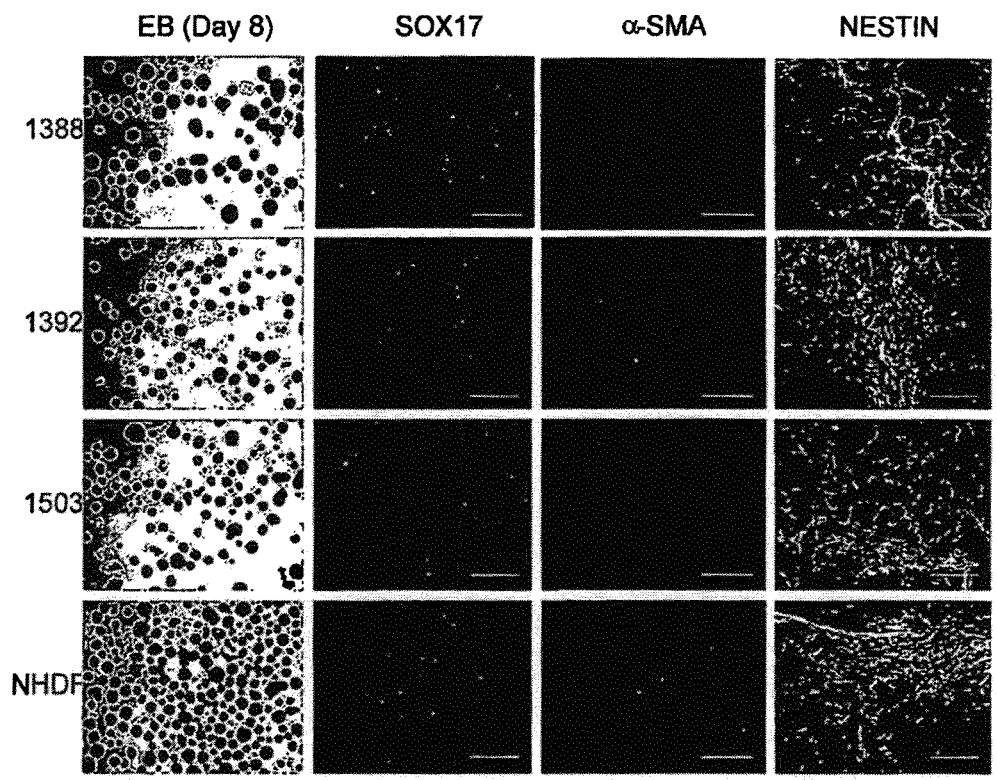
FIG. 7 shows micrographs of embryoid bodies formed from the respective iPS cells, and micrographs of immunostaining of cells differentiated from iPS cells in vitro. Sox17 and α-SMA-positive cells are shown in red, and NESTIN-positive cells are shown in green. Nuclei were stained with Hoechst 33342 and are shown in blue. The bar represents 100 μm.

To investigate pluripotency of the iPS cell clones established in Example 2, in vitro differentiation was carried out. From the iPS cell clones established on the fibroblasts from which they were derived, embryoid bodies were formed by suspension culture. Sixteen days after the differentiation, Sox17 (endoderm), α-smooth muscle actin (α-SMA, mesoderm) and NESTIN (ectoderm)-positive cells were observed (FIG. 7).

Figure 8:
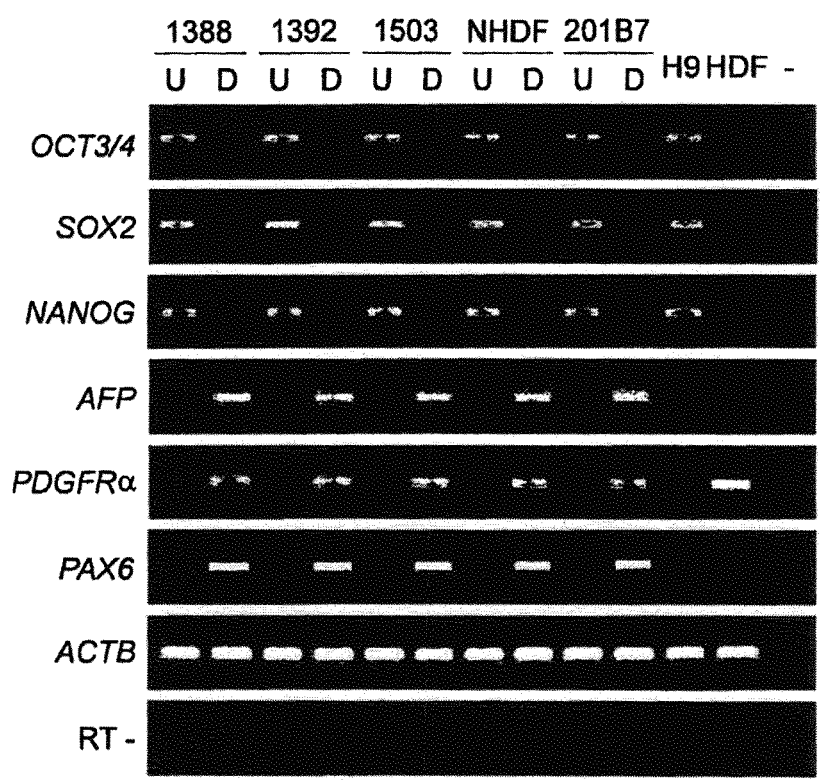
FIG. 8 is a photograph showing RT-PCR analysis of undifferentiation and differentiation markers after culturing of the established iPS cells of each type on feeders to keep undifferentiated (U) or to differentiate to form embryoid body (D). As controls, HDF and H9 are shown.

Subsequently, the iPS cells of each type established were cultured on feeder cells and allowed to maintain undifferentiation (U) or to differentiate to form embryoid bodies (D), and expressions of the respective differentiation markers and undifferentiation markers were investigated by RT-PCR. As a result, decrease in undifferentiation markers such as Oct3/4, Sox2 and Nanog and increase in other differentiation markers such as AFP, PDGFRa and Pax6 were observed (FIG. 8). Further, in addition to this, the iPS cells may be administered to testis to confirm formation of teratoma.

Figure 9:
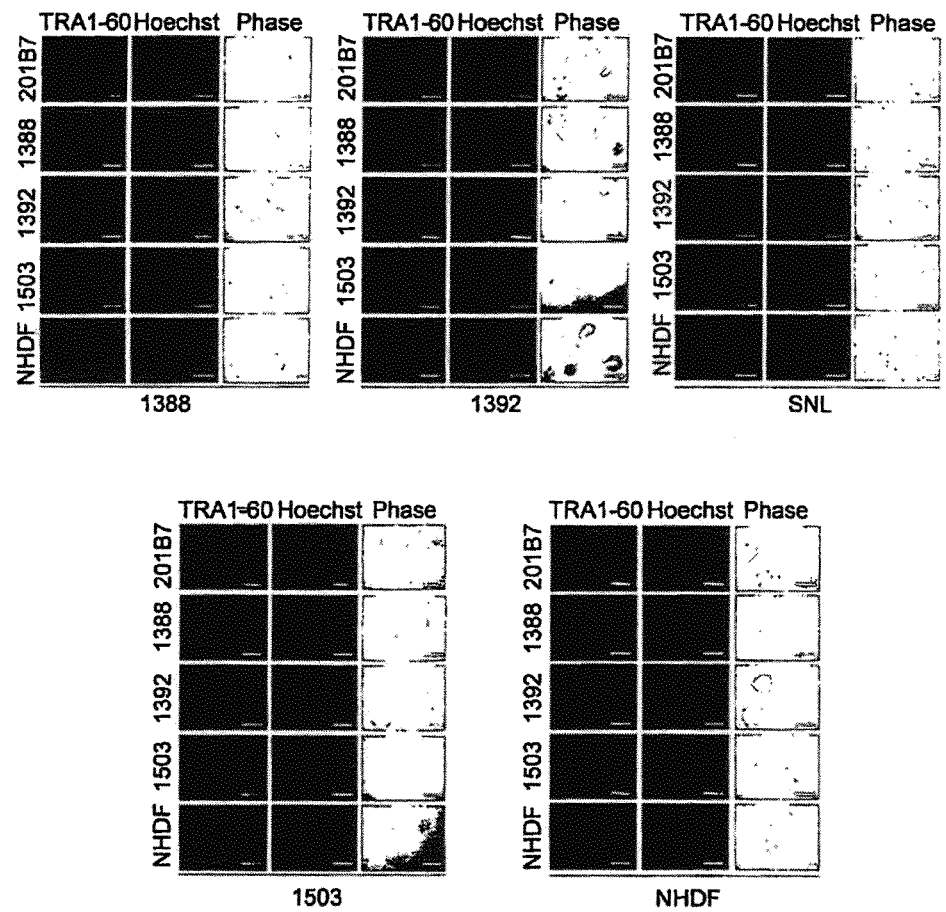
FIG. 9 shows micrographs of respective iPS cells (201B7, 1388, 1392, 1503 and NHDF) co-cultured with the respective human fibroblasts or SNL as feeder cells. TRA-1-60-positive cells are shown in red, and the Hoechst 33342 staining at the center shows nuclei. The bar represents 200 μm. "Phase" indicates an image formed by superimposition of the both images.
Figure 10:
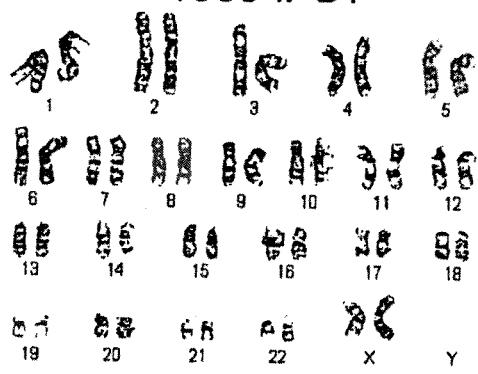
FIG. 10 shows results (micrograph) of analysis of the karyotypes of respective iPS cells (1388, 1392, 1503 and NHDF) co-cultured with the respective human fibroblasts as feeder cells.
Figure 10:
Figure 10:
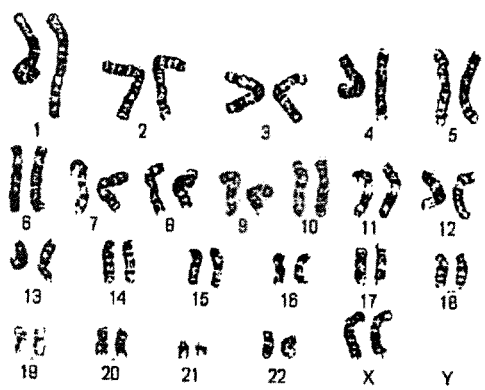
Figure 10:

Further, to confirm whether the iPS cells of each type can be cultured also on human fibroblasts derived from another source (another individual), the iPS cells of each type were cultured using the human fibroblasts of each type or SNL as feeder cells. The iPS cells were stained with TRA-1-60 antibody 6 days after the beginning of the culture, and the number of positive cells was measured. As a result, it was shown that not less than 80% of the colonies were undifferentiated cells even when the culture was carried out using the human fibroblasts derived from another source (FIG. 9). Further, when the karyotypes of the thus cultured iPS cells were analyzed, no abnormal chromosomes were found (FIG. 10). Thus, it was found that human fibroblasts were confirmed to be useful as feeder cells when iPS cells are cultured.

The invention claimed is:

1. A method for producing human induced pluripotent stem cells from human fibroblasts, comprising the steps of:
   a) introducing nuclear reprogramming factors to a population of human fibroblasts, wherein said nuclear reprogramming factors comprise the Oct 3/4 gene, a gene from the Sox gene family, and a gene from the Klf gene family;
   b) culturing the population of human fibroblasts under conditions for human embryonic stem cells, without feeder cells so as to produce colonies of human iPS cells on cells exhibiting a fibroblast-like morphology and
   c) selecting said colonies of human iPS cells.

2. The method according to claim 1, wherein said nuclear reprogramming factors comprise the Oct3/4 gene, Sox2 gene, and Klf4 gene.

3. The method according to claim 1, wherein said method further comprises culturing colonies obtained by step c) with a second population of mitotically inactivated human fibroblasts from the same individual as the first population in which the nuclear reprogramming factors are not introduced.

4. The method according to claim 3, wherein said second population of human fibroblasts is treated with mitomycin C or γ-ray irradiation.

5. The method according to claim 3, wherein said second population of human fibroblasts is the same human fibroblasts as the population of human fibroblasts that were used to produce iPS cells.

* * * * *